United States Patent [19]

Jung

[11] Patent Number: 5,184,630
[45] Date of Patent: Feb. 9, 1993

[54] HAIR DEODORIZING COMPOSITIONS AND PROCESS FOR USING

[75] Inventor: Mary L. Jung, Millwood, N.Y.

[73] Assignee: UOP, Des Plains, Ill.

[21] Appl. No.: 864,245

[22] Filed: Apr. 6, 1992

[51] Int. Cl.$^5$ .......................... A61K 7/06; A61K 7/08
[52] U.S. Cl. .................................. 132/202; 132/204; 424/70; 424/71
[58] Field of Search .............. 132/202, 203, 204, 209; 424/70, 71

[56] References Cited

U.S. PATENT DOCUMENTS 4,738,841  4/1988  Pigiet ..................................... 424/71

Primary Examiner—Gene Mancene
Assistant Examiner—Frank A. LaViola
Attorney, Agent, or Firm—Thomas K. McBride; Richard G. Miller

[57] ABSTRACT

Treatment of human or animal hair for purposes of waving, straightening or softening using compositions containing thioglycolic acid compounds commonly leave an undesirable odor due to the presence of residual trace amounts of the thio compound. The compositions of the present invention contain siliceous crystalline molecular sieves either as the sole active ingredient or in combination with hair conditioners. When applied to hair containing conventional, acid or soft wave hair perming solutions, the molecular sieve constituent effectively adsorbs and holds the residual odor-causing thioglycolic acid compound so that its odor is reduced to below its olfactory detection level threshold.

5 Claims, No Drawings

HAIR DEODORIZING COMPOSITIONS AND PROCESS FOR USING

FIELD OF THE INVENTION

The present invention relates to treatment of human or animal hair, and more particularly to the deodorization of such hair which contains residual thioglycolic acid compounds as a consequence of prior treatment to effect waving, straightening, softening and the like. Deodorization is effected by applying a composition containing a crystalline siliceous zeolitic molecular sieve material having a framework $Si/Al_2$ ratio of at least 18 and having an adsorptive capacity for water of not greater than 10 weight percent when measured at 25° C. and a water vapor pressure of 4.6 torr. Advantageously the molecular sieve-containing composition contains additional hair-conditioning materials.

BACKGROUND OF THE INVENTION

A considerable number of compositions have been proposed and are currently marketed for the purpose of modifying the configuration of hair shafts to achieve the appearance desired by hair styling. The modification, in the main, alters the hair shaft by disrupting the disulphide cross-linkages in the keratin fibers, thereby permitting normally wavy hair to be made less wavy or allowing normally straight hair to be reshaped into a waved or curled configuration. A number of particular chemical compounds have been employed, but by far the most commonly used compound is thioglycolic acid or the ammonium, sodium, calcium and potassium salts of thioglycolic acid. The compounds appear to reduce the disulfide cross-link to sulfhydryl groups which allows an easier reorientation of the keratin fibers of the hair shaft. Other thiols and mercaptans can accomplish the necessary cleavage of the disulfide cross-link, but in general are less suitable for the purpose.

Although effective in altering the chemical structure of the hair shaft, the aforementioned organic sulfur-containing compounds are characterized by a generally offensive odor. This is particularly true of the thioglycolic acid compounds. While the odor is tolerable over the relatively short period of the hair treatment, it is extremely difficult to remove these sulfur-containing compounds from the hair and scalp following the treatment to a level where the odor is not detectable.

The common method for overcoming the residual odor problem is to apply a masking fragrance to the hair during and/or after the treatment. Such fragrances must, of necessity, be rather strong, and for that reason can also be objectionable to some people. In U.S. Pat. No. 4,738,841, issued Apr. 19, 1988, to V. P. Pigiet, another means is proposed for reducing the objectionable odor of thioglycolic acid compounds during hair treatment. This means comprises decreasing the amount of thioglycolic acid required by incorporating a thioredoxin or similar dithiol peptide into the treating composition which acts synergistically with a thioglycolic acid compound to disrupt the disulfide bond of hair keratin. This technique doubtlessly decreases the odor level during the hair treatment, but has less effect in lowering the post-treatment level of residual thioglycolic acid compound.

SUMMARY OF THE INVENTION

The present invention provides compositions comprising highly-siliceous zeolitic molecular sieve crystals which when applied in appropriate amounts to hair containing malodorous sulfur-containing compounds effectively reduces the undesirable odor to levels below the detection threshold of the human sense of smell. Advantageously the zeolitic molecular sieve has at least about 90 percent of its framework structure composed of $SiO_2$ tetrahedral oxide units, has pore diameters of at least about 5.5 Angstroms and a capacity for adsorbed water of not greater than 10 weight percent when measured at 25° C. and at a water vapor pressure of 4.6 torr. The compositions can consist of the zeolite crystals or be combined in a powderous mixture with other ingredients which facilitate application or provide additional conditioning or grooming benefits to the hair, or in a flowable liquid-based composition such as a cream or mousse. The invention also includes the deodorization process utilizing the aforementioned compositions.

DETAILED DESCRIPTION OF THE INVENTION

The molecular sieves suitably employed in the compositions of the present invention include any of the crystalline aluminosilicate molecular sieves well known in the art in which at least about 90, and preferably at least 95, percent of the framework tetrahedral oxide units are $SiO_2$ tetrahedra and which have a sorptive capacity for water at 25° C. and 4.6 torr of less than about 10 weight percent, preferably less than about 6 weight percent. In the case of aluminosilicate molecular sieves, the framework $SiO_2/Al_2O_3$ molar ratio is at least 18 and is preferably at least 35. Molecular sieve zeolites having framework molar $Si/Al_2$ ratios of from 200 to 500 are particularly suitable. Many of the synthetic zeolites prepared using organic templating agents are readily produced in a highly siliceous form. In many instances the reaction mixtures can be especially free of aluminum-containing reagents. These zeolites are markedly organophilic and include ZSM-5 (U.S. Pat. No. 3,702,886); ZSM-11 (U.S. Pat. No. 3,709,979); ZSM-35 (U.S. Pat. No. 4,016,235); ZSM-23 (U.S. Pat. No. 4,076,842); and ZSM-38 (U.S. Pat. No. 4,046,859) to name only a few. It has been found that the silica molecular sieves known as silicalite and F-silicalite are particularly suitable for use in the present invention and are thus preferred. These materials are disclosed in U.S. Pat. Nos. 4,061,724 and 4,073,865, respectively. To the extent the aforesaid siliceous sieves are synthesized to have $SiO_2/Al_2O_3$ ratios greater than 35, they are frequently suitable for use in the present compositions without any additional treatment to increase their degree of hydrophobicity. Molecular sieves which cannot be directly synthesized to have both sufficiently high Si/Al ratios and/or degree of hydrophobicity can be subjected to dealumination techniques, fluorine treatments and the like, which result in organophilic zeolite products. High-temperature steaming procedures for treating zeolite Y which result in hydrophobic product forms are reported by P. K. Maher et al, "Molecular Sieve Zeolites," Advan. Chem. Ser. 101, American Chemical Society, Washington, D. C., 1971, p. 266. A more recently reported procedure applicable to zeolite species generally involves dealumination and the substitution of silicon into the dealuminated lattice site. This process is disclosed in U.S. Pat No. 4,503,023, issued Mar. 5, 1985, to Skeels et al. Halogen or halide compound treatments for zeolites to increase their hydrophobicity are disclosed in U.S. Pat. Nos. 4,569,833 and 4,297,335.

In the case of the aluminosilicates or silica polymorphs produced using large organic templating ions such as tetraalkylammonium ions, it is frequently necessary to remove charge balancing organic ions and any occluded templating material in order to permit their use in adsorption processes.

It should be pointed out that with respect to the hydrophobic aluminosilicates it is the framework $SiO_2Al_2O_3$ ratio which is important. This is not necessarily the same ratio as would be indicated by conventional wet chemical analysis. Especially is this the case when dealumination has been accomplished by high temperature steaming treatments wherein aluminum-containing tetrahedral units of the zeolite are destroyed, but the aluminum values remain, at least in part, in the zeolite crystals. For such zeolite products resort must be had to other analytical methods such as X-ray and NMR. One such steam-treated zeolite Y composition, known in the art as LZ-10, has been found to be particularly useful in the compositions of the present process, especially when utilized in combination with the silica polymorph silicalite. The process for preparing LZ-10 is described in detail in U.S. Pat. No. 4,331,694. When applied to the sequestration of odors due to organic sulfur-containing compounds such as thioglycolic acid, a benefit appears to be obtained by such a combination of molecular sieves in all proportions, but each type of adsorbent is preferably present in an amount of at least 10 percent based on the total weight of the two adsorbents (hydrated weight basis).

As synthesized the molecular sieve particles have, in general, sizes of about 0.5 to about 6.0 micrometers. The particles are most frequently agglomerates having sizes in the range of 10 to about 20 micrometers. Molecular sieve particles in this range, i.e., 0.5 to 20 micrometers or even larger, are all suitably utilized in forming the present compositions. It is preferred, however, that the particles are within the size range of 1.5 to 6.0 micrometers.

The molecular sieve particles can be topically applied to the hair and scalp being treated to remove the odor of the sulfur-containing compound or compounds in its undiluted and powderous form. Since, however, the molecular sieve is highly effective for the intended purpose, uniform application of sufficient quantities to deodorize the area is facilitated by incorporating the molecular sieve crystals in a composition containing inert diluents, liquid dispersion media or conventional substances used to condition hair.

If it is desired to employ a dry powderous composition, the molecular sieve can be admixed with such diluent/agglomerating agents as starch, silica powders, grain flours, wood flour, talc, pumice, clays, calcium phosphates and the like. Usually the molecular sieve constitutes from about 1 to about 10 weight percent of the overall mixture.

It is particularly preferred that the molecular sieve be dispersed in a liquid, advantageously aqueous, medium, and applied to the hair as a gel, cream, lotion, mousse and the like. These compositions can comprise water as the major constituent and suspension medium into which the molecular sieve particles are suspended by means of suspension aids. Such suspension agents include hydrophilic colloidal dispersions of clays and those polyelectrolytes which function primarily to lower the zeta potential of the dispersed phase and thus lessen the tendency of the molecular sieve particles to agglomerate, and viscosity enhancers such as hydroxyethyl cellulose and carboxypolymethylene, available commercially under the trademarks Natrosol 250MR (Aqualon Company) and Carbopol 941 (B. F. Goodrich Company), respectively.

Especially useful as dispersion or suspension agents are the colloidal magnesium aluminum silicate clays such as those commercially available under the trademarks Laponite (LaPorte PLC, Waverly Mineral Prod. Co.) and Veegum (R. T. Vanderbilt Company). The colloidal magnesium silicates are refined from the natural minerals commonly referred to as smectite, montmorillonite, hectorite or macaloid clays. These clay minerals have a sodium magnesium-fluoro-litho-silicate structure and are characterized by an expanding lattice structure which swells when heated and dispersed in water. The magnesium, lithium and fluorine are inaccessibly located within the lattice structure and are, therefore, not water soluble or exchangeable. Laponite is a synthetic magnesium silicate, having properties similar to natural smectites. This synthetic silicate contains exchangeable lithium and calcium cations in place of the aluminum present in natural smectite clays. As used herein, these clays, both synthetic and naturally occurring, are identified by the term magnesium silicates of the smectite type or, alternatively, as magnesium silicates having the smectite structure.

Other commercially available polyelectrolyte suspension aids, which are somewhat less effective in lowering the zeta potential of aqueous suspensions of high-silica zeolites than the aforementioned smectite clays, include a copolymer of sodium acrylate and acrylamide (available commercially from Allied Colloids Company under the trademark Percol 726 and Percol 727); the sodium salt of a polymerized naphthalene sulfonic acid and the sodium salt of a polymerized alkyl naphthalene sulfonic acid (both available commercially under the trademarks Darvan No. 1 and Darvan No. 9, respectively, from R. T. Vanderbilt Company); a penta sodium salt of aminotri(methylene phosphonic acid) sold commercially by Monsanto Chemical Company under the trademark Dequest 2006; and the sodium salt of a polymeric carboxylic acid, a polyelectrolyte with an anionic charge similar to Dequest 2006, sold by Allied Colloid Company under the trademark Dispex N-40. These other polyelectrolytes are generally not effective over long periods of time and are preferably employed in combination with viscosity enhancing agents to counteract the effects of Stokes Law Further, non-surfactant type hydrophilic colloids that coat the molecular sieve particles can also be employed, but they are, in general, not entirely effective to prevent settling of the zeolite particles in aqueous trademark of GAF Chemical Company) and Resyn 28-1310 and Resyn 28-2930, both trademarks of National Starch Company. Gantrez AN is a copolymer of vinyl ether and maleic anhydride. It is a water-soluble polymeric anhydride that slowly hydrolizes in the presence of water to form the free acid. Addition of small quantities of alkali aids solution, but must be controlled since it results in dramatic increase in viscosity of the dispersed aqueous phase. PVM/MA copolymer acts as a protective colloid by adsorbing onto the surface of solids that are to be dispersed and suspended. It is available in several molecular weight ranges. The grades 119 and 169 reflect molecular weights ranging from 20,000 to 67,000. Resyn 280-1310 is a carboxylated vinyl acetate copolymer which must be neutralized from ethanol solutions to achieve water solubility. When neutralized with an amino hydroxy compound such as AMP (2-amino-2-methyl-1-propanol), water solubility occurs. Coating suspended particles in hydroalcoholic vehicles with the neutralized Resyn can prevent coalescence of solid particles by the process of adsorption. The Resyn in this case acts as a protective colloid to prevent contact with other solid particles. Resyn 28-2930 is a terpolymer of vinylacetate, crotonic acid and neo-decanoate. As with Resyn 28-1310, ethanol solutions of this polymer must be neutralized with AMP to achieve water solubility.

Anionic polyelectrolytes such as CMC are advantageously employed in combination with the colloidal magnesium aluminum silicates described above for suspending high-silica zeolites in aqueous media. CMC, an alkali metal salt of the carboxymethylether of cellulose, is an anionic water-soluble polymer derived from cellulose by the reaction of alkali metal chloracetate with alkali cellulose. It is classified as an anionic polyelectrolyte and is commercially available predominantly as the sodium salt. The properties of CMC can vary considerably, the principal determinants being the degree of substitution (DS) and the degree of polymerization (DP) or chain length. The DS is defined as the average number of carboxymethyl groups introduced, i.e., substituted for hydroxyl groups per anhydroglucose unit in the cellulose. The DP is determined by the chain length of the starting cellulose which can be as high as 5000. The DP is reflected in the viscosity of the CMC solution and as the DP increases the viscosity increases. CMC is commercially available in viscosities from about 3000 cP in 1% solution to 17 cP in 2% solution, corresponding to a DP range of from about 1000 to 200.

In addition to the aforesaid constituents of the vehicle in the present compositions, a number of other materials can be added to provide cosmetic and/or formulation functionality. These include propylene glycol, hexylene glycol and 1,3-butylene glycol, all of which serve to act as rheological modifiers. Colorants and pigments are suitably incorporated into the present compositions, as are fragrances which are compatible with, i.e., not eliminated by the activity of, the high-silica zeolites also present. Lower alcohols such as ethanol and they do not cause precipitation of the CMC constituent, if it is present. Fungicides, bactericides and medicinal or therapeutic materials can also be present. When antimicrobial or preservative agents are included in the compositions, it should be noted that not all such agents are compatible with the high-silica zeolite constituent. It is believed that this incompatibility, i.e., ineffectiveness, is due, at least in part, to these substances being adsorbed into the internal pore system of the zeolite crystals and are thus limited in their contact with microorganisms present in the medium outside the zeolite particles. Accordingly, it is preferred to utilize as the biocidally active component a phenoxarsine-containing compound, preferably one that is soluble at least to a moderate extent in the glycol or aqueous media of the composition. Such compounds are well known in the art and include 10-chlorophenoxarsine; 10-bromophenoxarsine; 10-phenoxarsinyltrichloracetate; (10-phenylarsinyl)-n-octylxanthate; 10-methylphenoxarsine; 10-butylphenoxarsine; 10-phenylphenyloxarsine; (10-phenoxarsinyl) diisopropylphosphonate; and 10,10'-oxybisphenoxarsine. A particularly preferred phenoxarsine compound for use in the present compositions is cis-1-(3-chloro-2-propanyl) - 3,5,7 - triaza-1-azoniatricyclo (3.3.1.1[3,7]) decane halide, particularly the chloride or bromide, available commercially under the trade name Dowicil 200, or as quaternium-15.

A number of compositions suitable for use in the practice of the present invention are exemplified by those prepared in the following Examples.

EXAMPLE 1

The ingredients listed below, and in the proportions indicated, were combined to form a composition effectively used in the practice of the present invention.

|  | Wt. % |
|---|---|
| Laponite XLS | 1.00 |
| Laponite XLG | 0.50 |
| Distilled Water | 84.35 |
| Zeolite* | 5.00 |
| Stepanate SXS | 4.00 |
| Propylene Glycol | 5.00 |
| Dowicil 200 | 0.10 |
| Disodium EDTA | 0.05 |
|  | 100.00 |

*Equal parts by weight of zeolite LZ-10 and silicalite.

The composition was prepared by dispersing at room temperature the Laponite XLS and the Laponite XLG in distilled water using a high shear propeller mixer for a period of about 20 minutes. The zeolite particles were added and mixed under low shear conditions for about one hour, and then were added the propylene glycol and the Stepanate SXS (a sodium xylene sulfonate which acts as a hydrotrope coupling agent) and the mixing continued until the mixture was uniformly blended. Lastly, the Dowicil 200 and the disodium salt of ethylenediamine tetracetic acid (EDTA) were added and mixing continued for an additional 15 minutes. The formulation was dispensable as a mousse from an aerosol dispenser containing 81 percent by weight of the aforesaid formulation and 19 percent by weight isobutane propellant.

EXAMPLE 2

Using the same zeolite constituent as in Example 1, the following formulation was prepared by mixing together at room temperature the ingredients listed below and in the order in which they are listed.

|  | Wt. % |
|---|---|
| Distilled Water | 93.85 |
| Mackalene 316 | 2.00 |
| Merquat S | 2.00 |
| Zeolite | 2.00 |
| Dowicil 200 | 0.10 |
| Disodium EDTA | 0.05 |
|  | 100.00 |

In the formulation, the Mackalene 316 is a commercially available surfactant which serves to condition the hair having an advantage over some other cationic surfactants in that it rinses more readily from the hair and thereby prevents build-up, and the Merquat S, also commercially available, is a polyquaternium-7 high molecular weight cationic dimethyldiallyl ammonium chloride compound which contributes excellent lubricity, wet compatibility and luster to hair without build-up. This formulation is also dispensable as a mousse from an aerosol system using isobutane as the propellant.

EXAMPLE 3

(a) A base slurry was prepared by swelling 1.86 parts by weight Veegum in 89.9 parts by weight distilled water at a temperature of 65°-70° C. To this colloidal silicate system was added with mixing 0.93 parts by weight of sodium carboxymethyl cellulose (CMC 7LF). The mixing was continued for one hour and then the mixture was allowed to cool. When the temperature reached 50° C., 7.05 parts by weight hexylene glycol was added and the resulting composition mixed for 15 minutes. Finally 0.21 parts by weight Dowicil 200 and 0.05 parts by weight disodium EDTA were added and completely dispersed over the period of about 15 minutes.

(b) A zeolite-containing slurry was formed by the high shear mixing of 1.00 parts by weight Laponite XLS and 0.50 parts by weight Laponite XLG in 79.5 parts by weight distilled water for the period of about 20 minutes. Thereafter 5.0 parts by weight of the same zeolite constituent as employed in Example 1, above, was incorporated by low shear mixing for one hour and then an additional 5.0 parts by weight of the same zeolite was similarly incorporated. Thereafter 4.0 parts by weight Stepanate SXS and 5.0 parts by weight of propylene glycol were added and thoroughly blended into the composition.

(c) Equal parts by weight of the compositions of parts (a) and (b) were combined and 81 parts by weight were placed in an aerosol dispenser with 19 parts by weight isobutane. The mixture is found to be highly effective to remove from human hair the odor resulting from residual thioglycolic acid after a permanent wave treatment.

What is claimed is:

1. Composition suitable for use in eliminating the odor from human or animal hair due to the presence of a thioglycolic acid compound which comprises an aqueous suspension of particles of a crystalline zeolitic molecular sieve and a colloidal magnesium silicate having the structure of smectite, said zeolitic molecular sieve having $SiO_2$ tetrahedra as at least 90 percent of its framework tetrahedral oxide units, pore diameters of at least 5.5 Angstroms, and a capacity for adsorbed water not greater than 10 weight percent when measured at 25° C. and a water vapor pressure of 4.6 torr.

2. Composition according to claim 1 in which the colloidal magnesium silicate is a colloidal sodium lithium magnesium silicate having the smectite crystal structure.

3. Composition according to claim 2 which contains as additional ingredients a biocidally active agent, said agent being a phenoxarsine-containing compound, and an alkyl polyol rheological modifier.

4. Composition according to claim 1 wherein the phenoxarsine-containing compound is cis-1-(3-chloro-2-propanyl)-3,5,7-triaza-1-azoniatricyclo (3.3.1.1(3,7)) decane halide, and the alkyl polyol is a glycol selected from the group consisting of propylene glycol, hexylene glycol and 1,3-butylene glycol.

5. Process for deodorizing human or animal hair containing a thioglycolic acid compound residue which comprises applying to and contacting said hair with the composition of claim 1.

* * * * *